United States Patent [19]

Diesen

[11] 4,384,159
[45] May 17, 1983

[54] CATALYTIC DEHYDROHALOGENATION PROCESS

[75] Inventor: Ronald W. Diesen, Midland, Mich.

[73] Assignee: The Dow Chemical Company, Midland, Mich.

[21] Appl. No.: 357,508

[22] Filed: Mar. 12, 1982

[51] Int. Cl.³ .............................................. C07C 1/00
[52] U.S. Cl. .................................... 585/642; 570/226; 570/227; 570/229
[58] Field of Search ............... 570/226, 227, 229, 220; 585/642

[56] References Cited

U.S. PATENT DOCUMENTS 3,325,554  6/1967  Addy ................................... 585/642
3,896,182  7/1975  Young ................................. 570/226

FOREIGN PATENT DOCUMENTS 774158  12/1967  Canada ................................ 585/642
  2021   5/1979  European Pat. Off. ............ 570/226
1152021   5/1969  United Kingdom ................ 570/642

OTHER PUBLICATIONS

Olson et al., J. Catalysis, 61, 390 (1980).

*Primary Examiner*—Delbert E. Gantz
*Assistant Examiner*—A. Pal
*Attorney, Agent, or Firm*—Douglas N. Deline

[57] ABSTRACT

Saturated $C_{1-6}$ hydrochlorocarbons are dehydrochlorinated by contacting with ZSM-5 or silicalite zeolites at 200° C.–400° C.

4 Claims, No Drawings

CATALYTIC DEHYDROHALOGENATION PROCESS

BACKGROUND OF THE INVENTION

It is well-known that ethylenically unsaturated compounds can be produced from hydrochlorocarbons by means of a cracking or pyrolysis process by splitting off a molecule of hydrogen chloride. The cracking is accomplished in the absence of a catalyst by heating the hydrochlorocarbon in an inert atmosphere under high temperature and pressure. Usually a temperature in the range of about 500° C. to about 600° C. and a pressure of about 100 to 600 psig is used. The generation of such energy, of course, is expensive.

In European Pat. No. 2,021, a catalyst system comprising a zeolite which has been treated or reacted with a volatile Lewis acid was disclosed for the dehydrohalogenation of ethylene dichloride. Suitable catalysts include faujasite Y zeolite reacted with $TiCl_4$.

Synthetic activated divalent cation exchanged sodium zeolite A was disclosed in U.S. Pat. No. 2,920,122 as suitable in the dehydrochlorination of halo-substituted hydrocarbons. Specific examples included the conversion of tertiary butyl chloride to isobutene.

In U.S. Pat. No. 3,927,131, at column 4, lines 28–50, Table I, the use of a synthetic zeolite, SK-120, containing 10 percent rare earths of unspecified identity and 0.5 percent palladium in the dehydrohalogenation of aliphatic hydrochlorocarbons was disclosed. Temperatures employed were from about 400° C.–600° C.

Prior art processes for dehydrochlorination of hydrochlorocarbons have required that the synthetic zeolite be modified by reaction with Lewis acids or by exchange of divalent cations or incorporation therein of rare earths or noble metals. It would be desirable to provide a synthetic zeolite catalyst for the dehydrochlorination of hydrocarbons that does not require preparation or modification in the above ways.

Prior art processes have also obtained only limited conversions of hydrochlorocarbons thereby requiring long contact or reaction times or multiple passes of the hydrochlorocarbon over the catalyst bed.

It would be desirable to provide a catalyst system that allows the artisan to prepare dehydrochlorination products in relatively high conversions using reduced reaction or contact times without the formation of substantial quantities of by-products.

It would further be desirable to provide a catalyst system that will obtain the dehydrochlorination of hydrochlorocarbons at relatively mild reaction temperatures, thereby resulting in reduced energy consumption.

These objects and others that will become readily apparent to the skilled artisan have now been obtained according to the instant invented process.

SUMMARY OF THE INVENTION

It has now unexpectedly been found that improved conversion with less energy can be obtained by a process which comprises cracking or dehydrohalogenating hydrochlorocarbons by employing, as catalyst, a synthetic siliceous zeolite selected from the group consisting of ZSM-5 and silicalite. The use of the above zeolite cracking catalysts enables operation at temperatures far below that normally required with prior processes. Using the catalysts of the instant invention, the cracking process can be operated at a temperature in the range of about 200° C. to about 400° C., preferably from about 250° C.–350° C.

DETAILED DESCRIPTION OF THE INVENTION

The hydrochlorocarbons which may be dehydrochlorinated according to the present invention are $C_{1-6}$ saturated halogenated compounds such as 1,1- and 1,2-dichloroethane, 1,2- and 1,3-dichloropropane, 1,2,3-trichloropropane, 1,1,2-trichloroethane, 1,2-dichlorobutane and the like. Preferred are 1,1- and 1,2-dichloroethane which are used to prepare vinyl chloride.

The synthetic siliceous zeolites employed in the present invention are well-known in the art. ZSM-5 has been described in U.S. Pat. No. 3,702,886. Silicalite is further described as crystalline silica which after calcination in air at 600° C. for one hour produces a silica polymorph having a mean refractive index of $1.39 \pm 0.01$ and a specific gravity at 25° C. of $1.70 \pm 0.05$ g/cc. Silicalite has been described in U.S. Pat. No. 4,061,724. D. H. Olson et al., writing in *J. of Catalysis*, 61, 390–396 (1980) clarified the various zeolite structures related to ZSM-5 and concluded that highly siliceous pentasil structures such as silicalite have properties in conformity with and directly related to the level of aluminum content. Therefore, silicalite may be considered as an end member of a substitutional series, e.g., a substantially aluminum-free form of ZSM-5. For the above teachings, these references are herein incorporated by reference in their entireties.

These synthetic zeolites are employed in the instant invented process in either an alkali metal or hydrogen ion form. No special processing or preparation of the catalyst is required other than normal procedures such as calcining in order to remove organic residues.

It is to be understood that the zeolite catalyst is placed in the cracking reactor in such fashion as to allow the rapid passage of vapor or gas therethrough. The catalyst in the reactor may be either a fixed bed or a fluidized bed. The cracking step is done either neat or in an inert atmosphere, nitrogen being particularly good for this purpose. After the cracking reactor has been purged with nitrogen, the hydrochlorocarbon, preferably in gaseous form, is introduced into the reactor. When the hydrochlorocarbon comes in contact with the catalyst, the dehydrochlorination reaction or cracking proceeds smoothly and rapidly, converting the hydrochlorocarbon to the corresponding ethylenically unsaturated derivative and by-product hydrogen chloride.

The temperature in the cracker is maintained in the range of about 200° C. to about 400° C. Temperatures lower than 200° C. may be employed or one may use temperatures higher than 400° C. However, optimum results are obtained when operating within the temperature range given above.

While the cracking reaction may be operated at atmospheric pressure, or slightly below, it is preferred in the present invention to operate at superatmospheric pressure. A pressure anywhere up to about 100 atmospheres is satisfactory. At higher pressures cracking of the hydrochlorocarbon into undesirable chlorohydrocarbon by-products, such as $CCl_4$, etc., may occur. However, when using superatmospheric pressure, less cooking or carbon formation tends to occur. Periodically the reactor is shut down and the carbon or coke formation, if any, is removed, usually by burning off, that is, heating the reactor at a high temperature in the presence of oxygen or air. Usually a temperature in the range of about 300° C. to about 700° C. is sufficient to remove the coke formation.

The reaction or contact time of the hydrochlorocarbon with the catalyst in the reactor can be varied. The contact time necessary between the hydrochlorocarbon and catalyst to promote the desired dehydrochlorination reaction is obtained by controlling the space velocity of the gaseous material passing through the reaction zone. The contact time is dependent upon several factors, namely, the scale of the operation, the quantity of catalyst in the reactor or cracker, and the type of reactor employed. For most reactors a contact time as high as about 75 seconds or more and as low as 0.5 second can be employed. If the contact time is too low the quantity of unreacted hydrochlorocarbon coming over is too high. On the other hand, if the contact time is too high, that is, much above 25 seconds, the impurities increase which makes it more difficult to recover the desired compound in a pure form. One can readily adjust the gaseous feed rate to obtain the optimum reaction or contact time for any particular type reactor.

The gaseous mixture that is withdrawn from the cracker or reaction zone can be passed directly to a condenser thus recovering the condensable materials and allowing the hydrogen chloride to pass overhead and recycling the same. Alternatively, the gases leaving the reaction zone can be cooled and subjected to fractional distillation under superatmospheric pressure, preferably at the same or lower pressure as that used for the cracking.

SPECIFIC EMBODIMENTS

The following examples are given to more specifically define the instant invention. It is understood that these examples are intended in an illustrative and not limitative sense.

EXAMPLE 1

A sample of Linde molecular sieve zeolite, S115 silicalite (lot 8251-1-2) (5.2g) was loaded into a glass reactor TM" diameter×4¼" length. The reactor was equipped with 2 thermocouples at approximately ⅓ and ⅔ of the reactor length. The reactor was calcined by heating to 450° C. for approximately 16 hours while purging with nitrogen.

After calcining, the reactor was cooled and liquid ethylene dichloride flow initiated at a rate of 1.3 cc/hr and a nitrogen flow of 25 cc/min at atmospheric pressure. The ethylene dichloride was vaporized by a preheater and mixed with the nitrogen stream in a 21-stage static mixer before passing into the catalyst bed maintained at 325° C. After attainment of steady-state conditions (about 1 hour), the mixture was sampled and analyzed before and after passing through the reactor by flame ionization gas chromatograph. The results indicated a 50 percent conversion of ethylene dichloride. The only products detected were vinyl chloride and ethylene (1–3 percent).

EXAMPLE 2

The reaction conditions of Example 1 were substantially repeated to obtain approximately 50 percent conversion of ethyl chloride to ethylene at 265° C.

EXAMPLE 3

The reaction conditions of Example 1 were substantially repeated to obtain approximately 50 percent conversion of 1,1,2-trichloroethane to 1,2-dichloroethylene at 225° C.

EXAMPLE 4

The reaction conditions of Example 1 were substantially repeated to obtain approximately 100 percent conversion of 1,1,2-trichloroethane to 1,2-dichloroethylene at 350° C.

EXAMPLE 5

The reaction conditions of Example 4 were substantially repeated to obtain approximately 75 percent conversion of ethylene dichloride to vinyl chloride.

What is claimed is:

1. A process for the dehydrochlorination of saturated $C_{1-6}$ hydrochlorocarbons comprising contacting the hydrochlorocarbon in the gaseous phase with a synthetic siliceous zeolite selected from the group consisting of ZSM-5 and silicalite.

2. The process of claim 1 wherein the dehydrochlorination is conducted at a temperature of about 200° C. to about 400° C.

3. The process of claim 1 wherein the dehydrochlorination is conducted at a temperature of about 250° C. to about 350° C.

4. The process in claim 1 wherein the saturated $C_{1-6}$ hydrochlorocarbon comprises 1,1-dichloroethane, 1,2-dichloroethane or mixtures thereof.

* * * * *

UNITED STATES PATENT AND TRADEMARK OFFICE
CERTIFICATE OF CORRECTION

PATENT NO. : 4,384,159
DATED : May 17, 1983
INVENTOR(S) : Ronald W. Diesen

It is certified that error appears in the above—identified patent and that said Letters Patent is hereby corrected as shown below:

Column 2, line 64, "less cooking or" should read -- less coking or --.

Column 3, line 14, "about 75 seconds" should read -- about 25 seconds --.

Column 3, line 42, "reactor TM" diameter" should read -- reactor 1/2" diameter --.

Column 4, line 46, "process in Claim 1" should read -- process of Claim 1 --.

Signed and Sealed this

Eighth Day of November 1983

[SEAL]

Attest:

Attesting Officer

GERALD J. MOSSINGHOFF
Commissioner of Patents and Trademarks